Figure 1:
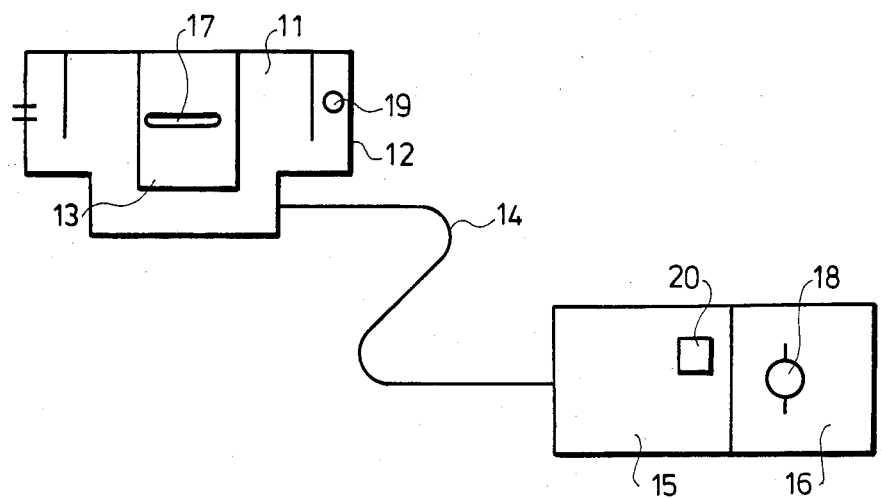

United States Patent [19]
Cséry et al.

[11] Patent Number: 4,644,550
[45] Date of Patent: Feb. 17, 1987

[54] LIQUID COOLED NEODYMIUM-PHOSPHATE GLASS-IMPULSE LASER PARTICULARLY FOR MEDICAL APPLICATIONS

[76] Inventors: Huba Cséry, Mihályfy E.u.26/B, H-1022 Budapest; Imre Czigány, Kardhegy u. 15., H-1116 Budapest; Zoltán Horváth, Galgóczy köz 7/A, H-1125 Budapest; Iván Kertész, Költöu.2-4., H-1121 Budapest; Norbert Kroó, Apáczai Cs.J.u.17., H-1052 Budapest; György Schmidt, Ó u. 38., H-1066 Budapest, all of Hungary

[21] Appl. No.: 690,496
[22] PCT Filed: Apr. 10, 1984
[86] PCT No.: PCT/HU84/00022
 § 371 Date: Dec. 11, 1984
 § 102(e) Date: Dec. 11, 1984
[87] PCT Pub. No.: WO84/04211
 PCT Pub. Date: Oct. 25, 1984

[30] Foreign Application Priority Data

Apr. 11, 1983 [HU] Hungary .............................. 1242/83

[51] Int. Cl.⁴ ................................................ H01S 3/17
[52] U.S. Cl. .......................................... 372/40; 372/35; 372/42; 372/10; 372/5
[58] Field of Search .................... 372/40, 39, 34, 92, 372/10-13, 35, 5, 69, 70, 42

[56] References Cited

U.S. PATENT DOCUMENTS 4,022,707  5/1977  Deutschbein et al. ................. 372/40
4,371,965  2/1983  Lempicki et al. ...................... 372/40

Primary Examiner—Leon Scott, Jr.
Attorney, Agent, or Firm—Toren, McGeady and Goldberg

[57] ABSTRACT

A fluid cooled neodymium phosphate glass impulse laser comprising a passive release circuit. The laser may be designed with reduced size so as to be portable and is mainly used in medicine particularly for eye operations, in spectroscopy, in cosmetics, teaching and microtechnology. The proposed laser comprises a resonator of small size having a fluid cooled laser body and which may be disassembled without detuning the resonator, a closed cooling circuit, a supply unit of small size and low consumption and an electronic circuit. The resonator comprises a thick passive release composed of a F/2 center-colored LiF crystal and having a characteristic passive transmission power of 70%, a high reflection coefficient mirror and a partially reflecting output mirror having a characteristic transmission of 60%. The active material is composed of a phosphate glass bar of small diameter, generally 3mm, having a high concentration of Nd ions, generally from 1.2 to $1.4 \times 10^{21}$ ions/cm³.

6 Claims, 4 Drawing Figures

LIQUID COOLED NEODYMIUM-PHOSPHATE GLASS-IMPULSE LASER PARTICULARLY FOR MEDICAL APPLICATIONS

The invention refers to a liquid cooled neodymium-phosphate glass-impulse laser with passive Q-switching, which can be fabricated to a small size, in a portable version and is mainly intended to be used in medicine, particularly in eye operations, furthermore in Spectroscopy, cosmetics, for teaching and in Microtechnology. The laser in the invention makes it possible to generate impulses in the $TEM_{00}$-mode with an impulse length lying below 20 ns, with an angular divergence amounting to less than 3 mrad, with energy boostable up to 50 mJ and with a maximum repetitive frequency, where the wave-length of the coherent light impulses is 1.054 $\mu$m.

The repetitive frequency of the laser impulses can be continuously varied up to the maximum values. The cooling of the laser head is accomplished with cooling liquid in a closed circuit. The device can be switched into the normal single phase power supply, its power consumption is typically 50 W, its overall weight approximately 2 kg.

The utilization of photocoagulators is known in eye therapy. Earlier on Xenon-lamp devices were used, whose long exposure periods (250–1000 ms) required a special anesthesia. Apart from that in most cases the focused light spot diameter (500–1000 $\mu$m) attainable at the retina is too large. In order to remove these disadvantages laser photocoagulators were developed, with which it is possible to concentrate the light beam of the laser upon a considerably smaller area, in the optimal case having a diameter smaller than 10 $\mu$m. Thus the desired biological action is achievable with impulse lengths smaller by several orders of magnitude, thus a special anesthesia is superfluous, it suffices to immobilize the head of the patient and to use means for dilating the pupils. For the successful treatment 1 to 5% of the energy of the light impulse of a Xenon-lamp is sufficient, often even a considerably smaller amount of energy.

In the previous phase of utilization ruby lasers functioning in impulse operation were primarily used, today on the contrary glass lasers designed with ionized Ar or Kr operating continuously are in wide use. With these the exposure periods are comparatively long, of the order of magnitude of 0.1 s, but their light can be focused relatively well. The disadvantage: since the exposure time is short in relation to the operating period, the light energy radiated by the laser is utilized only to a small extent.

Because the energy of the laser impulses utilized for the treatment—and with this also the undesirable side effects—can be reduced by a reduction of the impulse duration, there can be observed in the last two years a growing interest in solid body lasers, primarily in Q-switched, or in mode synchronized Nd:YAG-lasers. The price of these equipments is, however, very high, together with a device for immobilizing the head of the patient and the aiming optics which focus the laser light on the desired spot of the eye, it is of an order of magnitude of 100 000 U.S. dollars. Their dimensions are, however, very large, thus their application is essentially possible only in stationary versions, because besides the considerable weight their current consumption is also very high and generally requires cooling from the existing water mains. Information about these systems can be found in the publications LASER FOCUS (February 1983) and LASERS AND APPLICATIONS (October 1982).

The aim of the present invention is the realiztion of such a laser, which excludes the above-mentioned disadvantages and the creation of an inexpensive, portable device, which can be plugged into the normal single phase power supply and comprises a closed circuit cooling system, which will have broad utilization particularly in eye therapy.

The invention is based on the finding that the Nd-ions can be introduced in high concentrations into the lithium phosphate glass, with which a 2–3 times higher efficiency of the laser function can be achieved on a wavelength of 1.054 $\mu$m with typically a 3–5 times smaller beam divergence, than with an Nd:YAG-laser. All this can be realized by means of a laser rod of small dimensions—typical diameter 3 mm, length 55 mm.

With the device thus fabricated laser impulses in the $TEM_{00}$-mode of the above-mentioned wavelength of 1.054 $\mu$m and duration of approximately 18 ns, a maximum energy of 50 mJ and a maximum repetition frequency of 8 Hz can be generated, if a passive Q-switch fabricated from a LiF crystal is used, whose transmission has been adjusted to corresponding values typically to 70 to 80% by changing the concentration of the F-centers produced by x-rays.

Based on this finding the task was given to develop a device with consideration of the following items:

The laser shall be of small size, easily transportable of small weight, easily installable on existing facilities.

The laser should have a flexible connection with the supply unit and the cooling system, where this connection comprises also the electrical and cooling lines. Therefore the electrical current supply should be of relatively low voltage, so that the shock hazard requirements are complied with.

The portable, everywhere utilizable version requires in addition to a line voltage of particularly 220 V (most medical lasers work on three phase voltage) also a closed cooling system, thus it is independent of the central water supply.

In the solution usual with F-solid state lasers the voltage appears immediately at the beginning of the prolonged charging period at the flash lamp, so that it can lose its charge because of the small, electrical transient disturbances. This could have incalculable consequences in case of medical interventions. A supply unit of such a sort has to be developed in order to prevent this, so that without a starting signal no voltage is applied to the flash lamp; in this way the possibility of an accidental laser impulse is eliminated, that is because the charging period is so short, that the charging process and the laser impulse occur practically simultaneously with the starting signal and the laser remains without voltage until the next charging signal.

By application of the above-mentioned findings a portable liquid cooled neodymium-phosphate glass-impulse laser, particularly for medical applications was developed having the following characteristics: it comprises a passive Q-switch, a resonator, liquid cooled laser head, a cooling system as well as a supply unit, wherein accordance with the invention the resonator is of small size, the laser head is removable without adjustment of the resonator, the cooling system is of a closed type, the supply unit is of small size and low power consumption, furthermore according to requirement electronics are provided for indication of the operating mode, the trouble spots, counting of the impulses, energy level measurement, checking etc., a frequency doubler and filter, furthermore the resonator comprises a thick passive Q-switch, designed as a LiF-crystal, colored with $F_2^-$-centers, with a passive transmission of typically 70%, a highly reflective exit mirror and a partially reflective exit mirror with a transmission of typically 60%, and the active material is a phosphate glass rod of small-typically 3 mm- diameter and high Nd-ion-concentration -typically 1.2 to $1.4 \times 10^{21}$ Ion/cm$^3$.

It is advantageous if a flash lamp, used here as a pumping source, and the laser rod are arranged in a glass tube, which has been coated with a reflecteive layer on the outside and through which flows a cooling liquid, typically distilled water.

The good replaceability of the pumping flash lamp can be achievable, if the resonator is designed as a unit removable without adjustment.

Since the device considered from the laser technology viewpoint, is intended for use by laymen and this, because of the aging of the flash lamp, pretty unstable operating mode of the solid state laser requires periodic adjustment, an option was provided for possible installation of monitoring electronics, which indicates in a simple manner what corrections have to be made with the control element for optimum operation.

The basic construction also permits later installation of a pilot light, malfunction indicators, laser impulse counters, frequency doublers and filter combinations and energy level indicators. These units can also be designed according to the known principles.

On the basis of size and price, we selected a flash lamp which has to be replaced after approximately 50,000 flashes (2 to 4 week operation in normal medical practice). The simple process of lamp replacement requires, however, also a laser design deviating from the usual: in this case the laser head can be simply lifted out of the laser for the purpose of lamp replacement, without disturbing the resonator, and can be as simply again put back in its place.

Figure 3:
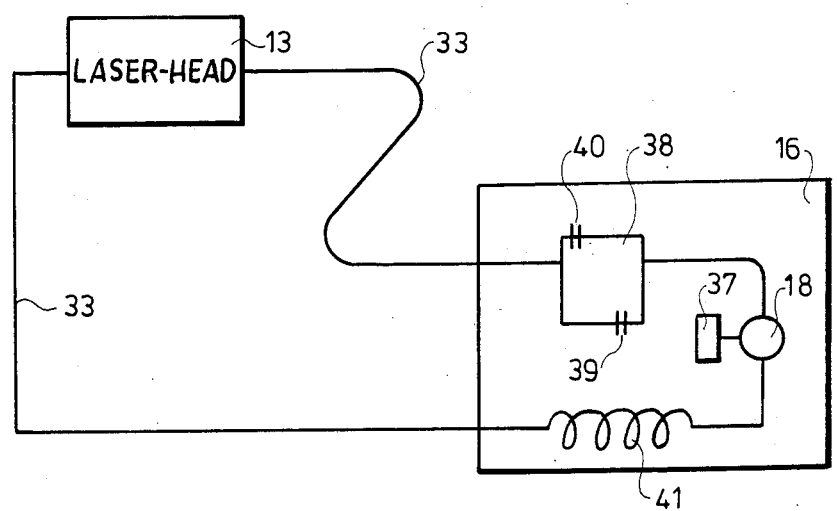
Figure 2:
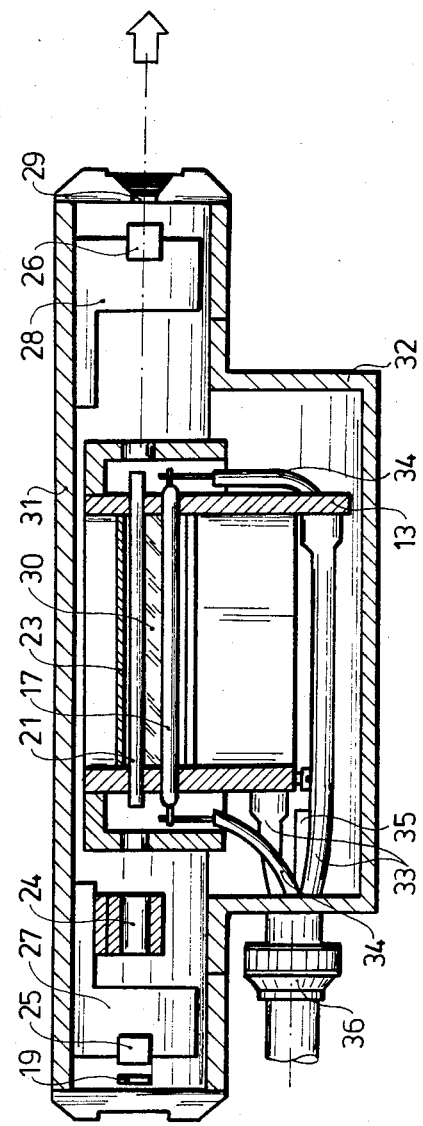
Figure 4:
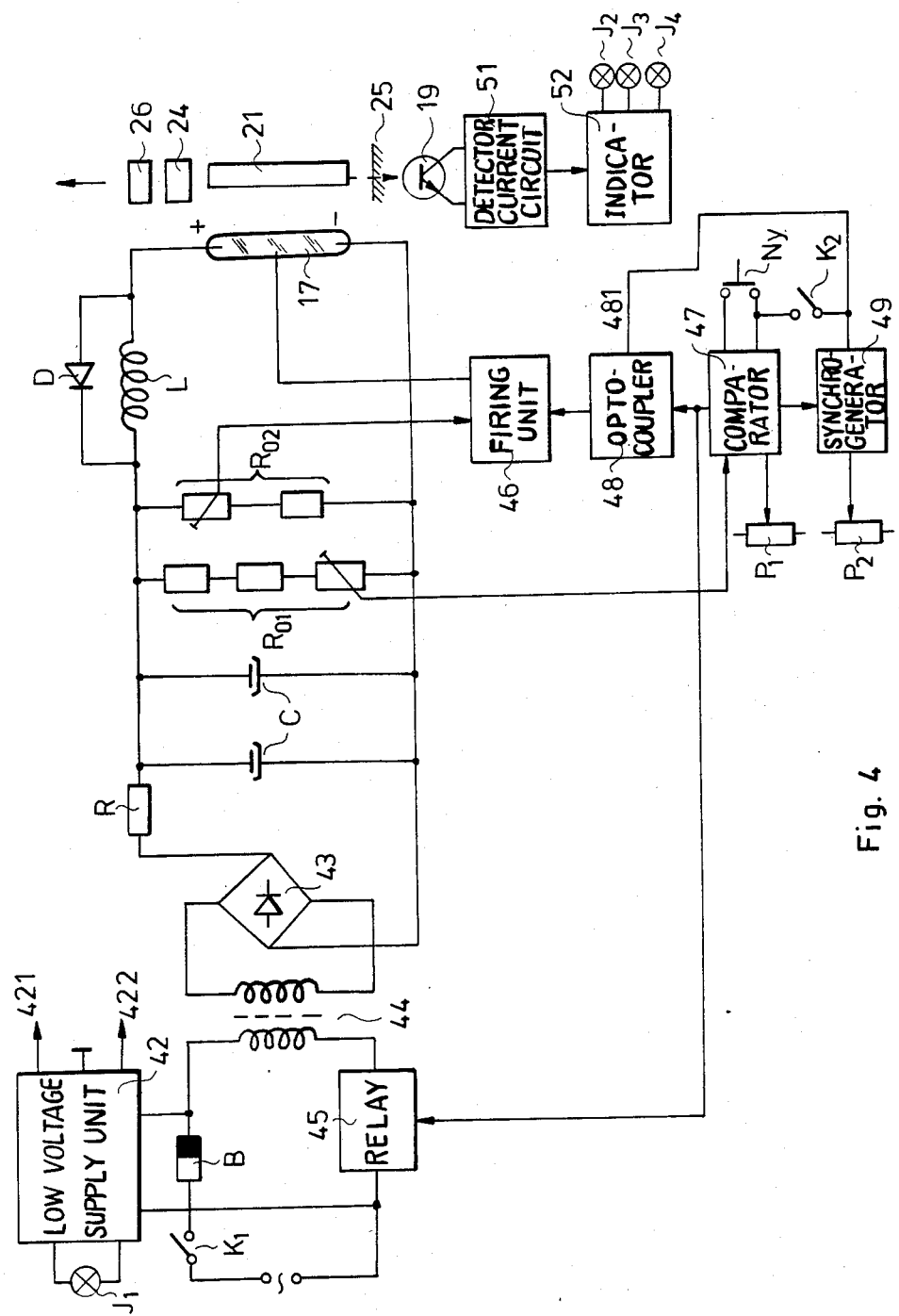

In the following the invention is explained with the help of the embodiment examples with reference to the enclosed drawings. It is shown on:

FIG. 1 a schematic presentation of the laser with cooling system and supply unit according to the invention;

FIG. 2 construction of the laser;

FIG. 3 schematic of the cooling circuit;

FIG. 4 block schematic of the supply unit.

The principal components of the device can be seen in FIG. 1. A laser 11, comprising a resonator 12 and an easily replaceable laser head 13, is connected through a conduit group 14, suitable for safely conducting electrical current and cooling liquid and installed in a flexible tube, with the supply unit 15, which is built together with a cooling system 16.

The supply unit 15 supplies energy to a Boitz lamp 17, a circulating pump 18, a photodetector 19 indicating the laser impulse and, when required, electronics 20.

The construction of the laser 11 can be seen in FIG. 2. A laser rod 21, serving as active element of the laser 11, with a diameter of 2 to 4 mm, typically 3 mm, and a flash lamp 17 are surrounded by a reflector 23 fabricated from a glass tube, whose outer surface is silverplated and, as protection against damage, is covered with an additional transparent varnish layer. The laser head 13 locks mechanically the flash lamp 17, the laser rod 21 and the reflector 23 and assures the entry and exit of the cooling liquid flowing in the glass tube of the reflector 23. The cooling liquid reaches the laser head 13 through an elastic pipe 33. Together with these pipes cables 34 of the supply voltage applied to the flash lamp 17 and cables 35 for the firing impulse are also led into the laser head 13 by means of a connecting screw 36.

A highly reflective blocking or pulsing mirror 25 and a partially reflective exit mirror 26 of a laser resonator built up from flat mirrors are attached in mirror retainers 27,28 of a layered construction, which are alignable by means of differential screws. The transmission of the exit mirror 26 lies between 55 to 65% typically at 60%. A Q-switch 24 fabricated from a LiF-crystal is attached at the mirror retainer 27 of the blocking mirror 25. The Q-switch 24 is thicker than 1 mm, suitably at least as thick as the diameter of the laser rod 21, its transmission amounts to 65 to 75%, typically 70%. The laser beam is emitted from a corresponding aperture 29 in the resonator, and the photodetector 19 of the operating indicator detects the weak light impulses penetrating the blocking mirror 25.

In case the laser 11 does not react to the impulse of the flash lamp 17, the photodetector 19 does not register a light impulse, in normal operation it registers one, in faulty operation two, in the case of correct operation—whose setting is supported by the indication reading of the operating mode—one therefore gets one impulse.

FIG. 3 shows a schematic arrangement of the cooling system 16, which apart from the laser head 13 and the elastic tubes 33 consists of a circulating pump 18 and the motor circuit 7 driving same, a heat exchanger 41, a surge chamber 38 for the cooling liquid and drain respectively feed valves 39, 40.

The cooling fluid is usually a slightly basic distilled water, whose basicity is typically regulated with trinate- hydrophosphate.

FIG. 4 shows a block schematic of the supply unit 15. A low voltage supply unit 42 and a solid state relay 45 are connected to the primary side of a high voltage transformer comprising a main switch $K_1$ and a fuse B. The secondary side of the high voltage transformer is on the one hand fed to the flash lamp 17, and on the other hand to a firing unit 46, both through a rectifier 43, resistor R, storage condensers C switched in parallel and a voltage divider $R_{01}$, $R_{02}$ and a diode D shunting an inductance L. The voltage divider $R_{01}$ is on the one hand connected through an optocoupler 48 and one output with the solid state relay, on the other hand connected to a synchronizing generator 49 through another output and a switch $K_2$ and also joined with a comparator equipped with a foot switch $N_y$. The synchronizing generator 49 is joined to a switch $K_2$ and also joined with a comparator equipped with a foot switch $N_y$. The synchronizing generator 49 is joined to a blocking input 481 of the optocoupler 48 and provided with a potentiometer $P_2$. The comparator is equipped with a potentiometer $P_1$. The output of the optocoupler 48 is led to the firing unit 46. The flash lamp 17 is optically coupled with the laser rod 21 inserted in between the Q-switch (with a subordinate exit mirror 26) and a blocking mirror (with a subordinate photodetector 19). The photodetector 19 is connected with a detector current circuit and through it with an indicating unit with lamps $J_2$, $J_3$ and $J_4$.

The low voltage supply unit 42 comprising a lamp $J_1$ assures at the outputs 421 and 422 the supply voltage for the electronics 20 and the motor 37 intended for the circulation. The electrical energy required for the discharge of the flash lamp 17 is supplied by the storage condensers C, whose charging occurs after the rectifier 43, with the help of the high voltage transformer 44. The resistance R protects the diodes of the rectifier 43 from the current pulses at the start of the charging process. An inductance L adjusts the discharge velocity of the condensers C through the flash lamp 17, meaning the duration of the flash. The diode eliminates the voltage transients at the inductance L. The charging process is switched on the primary side through the solid state relay 45 before the laser impulses. Otherwise no voltage is applied at the flash lamp 17. Control of the firing unit 40 occurs through the optocoupler 48 comprising a blocking input 481 in the form of single impulses or impulse series. The voltage reaching the flash lamp 17 and thus also its energy can be continuously varied by means of the potentiometer $P_1$ of the comparator unit 47. The comparator 47 monitors the voltage at the condenser C over the voltage divider $R_{01}$. The firing voltage of the firing unit 46 can be adjusted with the help of the voltage divider $R_{02}$. The repeat frequency of the laser impulses can be varied up to a maximum frequency of 8 Hz by adjustment of the potentiometer $P_2$ of the synchronizing generator 49 (frequency control unit). The verification of the operating mode is accomplished through processing of the signals of the photodetector 19 with the help of the detector current circuit 51 and the indicator unit 52 with its lamps $J_2$, $J_3$, $J_4$. Apart from a flash lamp impulse the lamp $J_2$ is illuminated if a laser impulse does not occur, the lamp $J_3$ is illuminated if one, the lamp $J_4$, if two laser impulses occur.

The laser 11 works in such a way that it requires only an alternating voltage of 220 V (if desired 110 V) from the outside and a power of typically 20 to 25 W. The device is switched on by means of the main switch $K_1$ which is indicated by the lamp $J_1$. This activates the low voltage supply unit 42. The energy required for the flash lamp 17 is adjusted with the potentiometer $P_1$, the repeat frequency with the potentiometer $P_2$. With the switching off of the switch $K_2$ and the operation of the foot switch $N_y$ individual impulses are generated. If the foot switch $N_y$ is operated, the storage condensers C are charged, and the flash lamp 17 receives voltage. Activated by the subsequent firing impulse the flash lamp 17 is fired, and if the laser 11 is correctly adjusted, meaning when the blocking mirror 25 and the exit mirror 20 are in the correct position, and the light of the flash lamp 17 is of sufficient intensity, the lamp $J_3$ of the indicating unit 52 is illuminated.

The laser resonator can be installed on any arbitrary optical system, typically on aiming devices, which are used in eye operations, for instance on the optical aiming devices or equipments for immobilizing the head of the photocoagulators, which utilize Ar - or Kr-Ion-lasers. In case of necessity one can mount a lamp each and optics, which focus these light sources in direction of the axis of the laser beam, meaning aiming axis, on both sides of the laser resonator. The light of the two light sources can be concentrated in the focal plane of these optics upon one point of the axis of the laser beam.

A characteristic feature of the laser according to the invention is its good beam quality ($TEM_{00}$-mode and no angular divergence). The beam can typically be focused upon a circle with a diameter lying below 10 μm.

The utilization areas of this device lie generally in eye surgery, but it can also be used in devices of Spectroscopy as excitation light source, in treatments with Acupuncture, in cosmetics and in Microtechnology (welding, aligning, etc.).

We claim:

1. A liquid cooled neodymium-phosphate glass pulsed laser, comprising a laser head (13) mounted on a base (32), said laser head (13) containing a flash lamp (17), a phosphate glass laser rod (21) and a cylindrical reflector (23) surrounding said flash lamp (17), the laser rod (21) is immersed in a cooling liquid flowing through said reflector (23), said laser rod (21) having a diameter of less than about 4 mm and a Nd-ion concentration of higher than about $1.2 \times 10^{21}$ ion/cm$^3$; a highly reflective rear mirror (25) and a partially reflective exit mirror (26) of about 60% transmission forming a laser resonator;

a passive Q-switch (24) comprising an $F_2^-$ color center doped LiF crystal disposed between said mirrors (25,26), said Q-switch (24) being thicker than 1 mm and having an initial transmission of about 60%;

said resonator with said mirrors (25,26) and said Q-switch (24) being placed in a resonator housing (31) which can be dismounted from the base (32) without adjustment of the mirrors (25,26); a flexible conduit group (14) connected to the lasen (11) wherein said flexible conduit group (14) includes pipes (33) for supplying the lasen (11) with the cooling liquid from a cooling system and cables (34) for supplying the laser (11) with current from a power supply unit (15).

2. The apparatus of claim 1, wherein said cylindrical reflector (23) is a glass tube coated externally with a reflective layer.

3. The apparatus of claim 1, wherein said cooling system (16) contains a liquid-air heat exchanger (41) and a circulating pump (18) driven by an electric motor (37).

4. The apparatus of claim 1, wherein said power supply unit (15) which powers the flash lamp (17) of the laser head (13) generates either single impulses or continuously adjustable periodic impulses of a frequency up to a maximum of 8 Hz, wherein the power supply unit (15) of the flash lamp (17) includes a fuse for protecting said however supply unit (15) against overvoltage, and wherein no voltage is applied to the lamp in case of absence of a start signal.

5. The apparatus of claim 1, wherein said mirrors (25,26) have retention means which are accurately alignable by differential screws.

6. The apparatus of claim 1, wherein said laser (11) further includes a built-in frequency doubling crystal which, together with special filters connected thereto, permits mixing in the emerging beam of infrared light of a wavelength of 1.054 μm with green light of a wavelength of 0.527 μm in any proportion.

* * * * *